United States Patent [19]

Kliegman et al.

[11] 4,431,437

[45] * Feb. 14, 1984

[54] BIOACTANT TRANSLOCATION AGENT

[75] Inventors: Jonathan M. Kliegman, Wayne, N.J.; James M. Williams, Cleburne, Tex.

[73] Assignee: GAF Corporation, New York, N.Y.

[ * ] Notice: The portion of the term of this patent subsequent to Jul. 21, 1998 has been disclaimed.

[21] Appl. No.: 223,452

[22] Filed: Jan. 8, 1981

[51] Int. Cl.$^3$ .................. A01N 57/00; A01N 43/36
[52] U.S. Cl. ........................................... 71/86; 71/79; 71/65; 71/94; 71/95; 71/115; 71/116; 71/117
[58] Field of Search ..................... 71/95, 86, 65, 79

[56] References Cited

U.S. PATENT DOCUMENTS

| | | | |
|---|---|---|---|
| 4,152,429 | 5/1979 | Hayakawa et al. | 424/222 |
| 4,238,219 | 12/1980 | Holm et al. | 71/95 |
| 4,251,259 | 2/1981 | Preziuso et al. | 71/117 |
| 4,261,726 | 4/1981 | Rusch et al. | 71/117 |
| 4,328,026 | 5/1982 | Kliegman et al. | 71/86 |
| 4,361,436 | 11/1982 | McCarthy et al. | 71/86 |

FOREIGN PATENT DOCUMENTS 2006740 5/1979 United Kingdom ................. 71/86

OTHER PUBLICATIONS

Takahashi et al., "Long-Lasting Gycethiord, etc."(1975) CA 84, No. 85633r, (1976).
Halliday, "Solvent System for Formulating, etc."(1971) CA 75, No. 109261k (1971).
Lubowe, "Nontoxic Pesticidal Compositions"(1958) CA 53, p. 9557 (h) (1959).

Primary Examiner—Glennon H. Hollrah
Attorney, Agent, or Firm—Marilyn J. Maue; J. Gary Mohr; Joshua J. Ward

[57] ABSTRACT

The present invention relates to novel agents for increasing the basipetal translocation of agricultural chemicals such as plant growth promoters, inhibitors, fungicides, insecticides or herbicides hereinafter referred to as "bioactants". The present agent comprises a mixture of N-heterocyclic amide and a haloethyl phosphonic acid in a mole ratio of between about 5:1 and about 1:10, employed in an inert carrier at a concentration between about 25 ppm to about 10,000 ppm which mixture can be applied to a plant prior to, or simultaneously with, the bioactant.

The translocating agent may be a mixture of the N-heterocyclic amide, e.g. N-methyl-2-pyrrolidone, and the haloethylphosphonic acid, e.g. 2-chloroethylphosphonic acid, it may comprise a mixture of said components with the complexed compound derived from the addition of said components or it may be the complexed compound per se.

4 Claims, No Drawings

BIOACTANT TRANSLOCATION AGENT

Extensive research has been carried out in search of herbicides for the control of perennial weed species, particularly deep rooted perennials, and annuals such as for example, Prosopis (mesquite), *Sorghum halepense* (Johnson grass), Arundo (giant reed), Convolvulus (bindweed), Cirsium (thistle), Cyperus (nutsedge), Centaurea (Russian Knapweed) and shallow rooted perennials such as Euphorbia (spurge), Pteridium (bracken fern), Agropyron (quackgrass), Digitaria (crabgrass), Cynodon (Bermuda grass), Helianthus (blue weed), Rumex (dock), Physalis (ground cherry), Lupinus (lupine), Acer (maple), Quercus (oak), Ascelepias (milkweed), Ipomoea (morning glory), Solanum (nettle, nightshade, silverleaf), Plantago (plantain), Ambrosia (ragweed), Rosa (multiflora), Sporobolus (smutgrass), Oxalis (wood sorrel), Franseria (bursage), Rhus (sumac, poison ivy) and many others. Many herbicides have been developed but are either highly selective to a particular plant species, climate sensitive or are very expensive to use. Also, it is recognized that only a portion of an applied herbicide is actually biologically engaged thus more efficient utilization is required. One of the causes for low efficiency is insufficient basipetal translocation of the herbicide to the root zone. For example, studies using $^{14}$C-(N-phosphonomethyl) glycine have indicated that less than 25% of the applied herbicide was translocated from treated leaves to the root in field bindweed. Hedge bindweed, Canadian thistle and wild buckwheat translocated only about 22%, 8% and 5% of the glyphosate herbicide; whereas field bindweed transferred only 3.5% from treated leaves, only half of which would be expected to reach the root zone. This work was reported in 1978 by C. L. Sandberg, Herbicidal Efficacy and Physiological Aspects of Glyphosate on Field Bindweed, Diss. Abst. Int. 39 (3)/1074–1075, phD. Thesis, Michigan State University.

Numerous chemicals or compositions thereof have been shown to influence the translocation characteristics of herbicides and especially the phenoxy auxin-like herbicides. However, very few of these chemicals have caused increased basipetal translocation. Most of the effects have been either to inhibit translocation or to enhance acropetal translocation. Morgan and Gousman (1966, Effects of Ethylene on Auxin Transport, Plant Physiology 41/45–52) showed that ethylene pretreatment would inhibit the transport of the auxin, indole-3-acetic acid, in excised stem segments. E. Basler (1977, Effects of Growth Regulators and Gibberellic Acid on 2,4,5-T Translocation, Weed Science 25/36–40) showed that pretreatment with ethephon (2-chloroethyl phosphonic acid), slightly increased acropetal translocation but had no significant effect on basipetal translocation of 2,4,5-T (2,4,5-trichlorophenoxy acetic acid) in intact bean seedlings. A similar pattern of activity was noted for 2-cyclopropyl-2-(p-methoxy-phenyl)-5-pyrimidine methanol. While ammonium ethyl carbamoyl phosphonate and morphactins greatly increased acropetal translocation to the young shoots and primary leaves they severely decreased translocation of 2,4,5-T to the roots. E. Basler and McBride, (1977, Effects of Coumarin, Juglone and Abscisic Acid on the Translocation of Auxin, Proc. Plant Growth Regulator Working Group 4/295–300), showed that pretreatment with coumarin inhibited 2,4,5-T translocation to the young shoots and primary leaves but had very little effect on translocation to the roots; Juglone enhanced acropetal translocation of 2,4,5-T but inhibited basipetal translocation. It was also found that abscisic acid applied simultaneously with the 2,4,5-T in stem tissue resulted in an increased 2,4,5-T translocation to the hypocotyl and roots of bean seedlings but that the effect was very ephemeral. Pretreatment with abscisic acid resulted only in inhibition of translocation. Binning, Penner and Meggitt (1971, The Effect of 2-chloroethylphosphonic acid on Dicamba Translocation in Wild Garlic, Weed Science 19/73–75) showed that ethephon caused some increase in basipetal translocation of Dicamba in wild garlic; however, it's effect was of short duration.

It is an object of the present invention to provide a translocating agent which promotes definative basipetal transport of a substance in plants.

Another object of this invention is to provide a translocating agent which increases the efficacy of various bioactants which bioactants can be used at lower rates to provide equal or greater efficacy than that required in the absence of the translocating agent.

Another object is to provide higher efficacy for herbicides resulting in enhanced control or pernicious weeds.

Still another object is to increase the efficacy of fungicides and insecticides to enhance control of plant disease causing organisms and insects.

Another object is to promote plant nutrition and growth development by increasing the efficiency of plant growth regulators and nutrients.

Still another object is to provide synergistic herbicidal plant response.

These and other objects will become apparent from the following description and disclosure.

According to this invention there is provided a translocating agent for use in conjunction with a bioactant such as a herbicide, insecticide, fungicide or a plant growth regulator. The translocating agent of the present invention comprises a mixture of a N-heterocyclic amide and a 2-haloethyl phosphonic acid, the complexed compound of said amide and acid or mixtures thereof. The translocating agent is suitably dissolved or dispersed in an inert carrier, such as a liquid carrier, e.g. water, ethanol, ethylether, chlorobenzene, benzene, toluene, a liquid paraffin, etc. or a dry particulate carrier e.g. talc, bentonite clays, diatomaceous earth, etc. in concentrations between about 25 ppm and 10,000 ppm, preferably between aout 50 ppm and about 5,000 ppm. Alternatively, the present translocating agent may be added directly to the formulation containing the bioactant prior to application.

The mole ratio of amide to acid present in the translocating composition may be varied within the range of from about 10:1 to about 1:5, preferably between about 0.5:1 and about 5:1. The mole ratio of the translocating agent to the chemical bioactant applied to the plant is generally within the range of between about 0.001:1 and about 1:1 preferably between about 0.05:1 and about 0.5:1.

The translocating agent, or composition containing said agent, may be separately applied to the plant up to 2 days before the application of the agricultural chemical. Alternatively, the translocating agent may be incorporated in the formulation of the bioactant and applied simultaneously.

Suitable bioactants which may be utilized in connection with the present translocating agent include the herbicides, such as 2,4,5-trichlorophenoxy acetic acid (2,4,5-T),
2,4-dichlorophenoxy acetic acid (2,4-D),
3,5-dichloro-o-anisic acid (Dicamba),
N-phosphomethyl glycine (Glyphosate),
sodium 5-(2-chloro-4-trifluoromethyl]-phenoxy)-2-nitrobenzene (Blazer),
3-cyclohexyl-6-(dimethylamino)-1-methyl-1,3,5-triazine-2,4-(1-H,3-H)dione (Velpar),
ammonium ethyl carbamoylphosphonate (Krenite),
3-(p-chlorophenyl)-1,1-dimethylurea (Monuron),
3-(3,4-dichlorophenyl)-1,1-dimethylurea (Diuron),
amine salt of [(4-chloro-o-tolyl)oxy] acetic acid (MCP Amine),
amino and alkyl-substituted amino salts of 2,4-D or 2,4,5-T.
3,5-dinitro-N,N-dipropylsulfanilamide (Oryzalin),
2-amino-3,5-dinitro-4-(dipropylamino)-benzo trifluoride (Redox),
2-(2,4-dichlorophenoxy)propionic acid (Dichlorprop),
N-(2,4-dimethyl-5-[(trifluoromethyl)sulfonyl]aminophenyl acetamide (Mefluidide),
4-amino-3,5,6-trichloropicolinic acid (Tordon 225E),
5-bromo-3-sec-butyl-6-methyluracil (Bromacil),
isopropyl n-benzoyl-n-(3-chloro-4-fluorophenyl)-2-aminopropionate (Barnon),
N-(4-chlorophenyl)-N'-methoxy-N'-methylurea (Aresin),
ammonium sulfamate (Ammate),
2,4-dinitro-6-sec-butyl-phenol (Dinoseb),
2,2-dichloropropionic acid (Dalapon),
2-chloro-2',6'-diethyl-N-(methoxymethyl)-acetanilide (Lasso),
3-amino-2,5-dichlorobenzoic acid (Amiben),
sodium salt of 2,5-dichloro-3-nitrobenzoic acid (Dinoben),
(3-chloro-4-chlorodifluoromethyl thiophenyl)-1,1-dimethylurea (Calercide),
4-tert-butylamino-2-chloro-6-ethyl-amino-s-triazine (Gardoprim),
Sodium N-1-naphthylphthalamate,
S-ethyl diisobutylthiocarbamate (Sutan)
S-ethyl dipropylthiocarbamate (Eptam)
S-ethyl-N,N-dipropylthiocarbamate/N,N-diallyl-1,1-dichloroacetamide (Eradicane)
4-Amino-6-(1,1-dimethylethyl-3-methylthio)-1,2,4-triazin-5(4H)-one (Metribrizin or Sensor)
2-chloro-4,6-bis(ethylamino)-s-triazine (Princep or Simazine)
α,α,α-trifluoro-2,6-dinitro-N,N-dipropyl-p-toluidine (Treflan)
Examples of suitable plant growth promoters and inhibitors include:
6-Benzylaminopurine (Benzyladenine),
N,N-Bis(phosphonomethyl)glycine (Glyphosine),
5-Chloro-3-methyl-4-nitro-1H-pyrazole (Release),
2-Chloroethyl trimethylammonium chloride (Chlormequat),
2-(3-Chlorophenoxy)propioic acid (3-CPA),
4-Chlorophenoxyacetic acid (4-CPA),
2-hydroxyethyl hydrazine (Omaflora),
1,2-Dihydro-3,6-pyridazinedione (Maleic hydrazide),
3-(2-[3,5-Dimethyl-2-oxocyclohexyl]-2-hydroxyethyl)glutaimide (Cycloheximide),
6-Furfurylaminopurine (Kinetin),
β-Hydroxyethylhydrazine (BOH),
1-Hydroxy-triacontane (Triacontanol),
3-Indoleacetic acid (IAA),
3-Indolebutyric acid (IBA),
Abscisic acid,
1-Naphthalene acetic acid (NAA),
2-Naphthoxyacetic acid (BNOA),
7-Oxabicyclo(2,2,1)-heptane-2,3-dicarboxylic acid monoalkylamine salt (Endothall),
Succinic acid-2,2-dimethyl hydrazine (SADH),
Gibberellic acid, ($GA_3$, $GA_{13}$),
2,3,5-Triodobenzoic acid (TIBA), ect.
Suitable systemic fungicides include:
Methyl-thiophanate (Topsin-M)
Tetrachloroisophthalonitrile (Bravo)
Methyl 1-(butylcarbamoyl)-2-benzimidazolecarbamate (Benomyl or Benlate)
n-Dodecylguanidine acetate (Dodine or Cyprex)
Thiobendazole (Mertect)
Examples of suitable insecticides include:
Octachloro-2,3,3a,4,7,7a-hexahydro-4,7-methanoindane (chlordane)
2,2-dichlorovinyl-O,O-dimethylphosphate (DDVP)
O,O-dimethylS-(1,2-dicarbethoxyethyl)phosphorodithioate (Malathion)
O,O-dimethylO-p-nitrophenyl phosphorothioate (Methyl Parathion)
O,O-diethyl-O-p-nitrophenyl phosphorothioate (Parathion).

The present agents promote the translocation of any of the above agricultural chemicals and are also beneficially employed to promote transfer of systemic pesticides, fungicides, herbicides and the like. It is to be understood that combinations of the above bioactants can be employed, as in available commercial formulations, and are generally applied at the rates recommended by the supplier of the bioactant. Increased benefits with herbicides can be realized when the translocating agent is separately applied to the plant from 2 hours to 2 days before application of the growth regulant and the plants are treated at an early stage of development, for example, up to the third foliate stage; although, it is to be understood that with other agricultural chemicals the present agents are also beneficially applied to more fully matured plants or plants in the senescence stage to obtain faster, more complete basipetal translocation of the bioactant to the lower stem, leaves, hypocotyl and root system. The pretreatment of plants with the present agent provides more efficient use of the bioactant so that a smaller amount of this chemical is required to achieve the desired result.

The present translocating agent is employed to particular advantage in the destruction of noxious plant species. Among the weed-like plants suitable for treatment with the present translocating agent and herbicide are leafy spurge, bracken fern, crown of klamath, bindweed, thistle, buckwheat, poison ivy, quackgrass, crabgrass, Bermuda grass, lilly of the valley, sheep sorrel, and plants of the allium species such as wild radish, garlic, and onion mesquite, etc. Generally, the plants species which can be treated by the present process include mono- and di-cotyledonous plantlife including trees, shrubs and smaller plants. The promotional growth of crops of the *gramineae, leguminosae, solanaceae, palmae, musaceae, cucurbitaceae, cruciferae, chenopodiaceae, malvaceae, rutaceae, bromeliaceae, euphorbiaceae, umbelliferae, liliaceae, rosaceae, rubiaceae, theaceae* and *sterculiaceae* families are also improved by the use of the present translocating agent when used in conjunction with bioactant.

The N-heterocyclic amide portion of the translocating agent is a 5- or 6-membered ring compound having one nitrogen atom per ring or a polymer* thereof, wherein the ring may be saturated or unsaturated. Preferred among these compounds are those having the formula

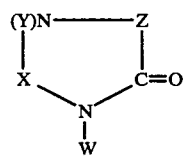

where n has a value of 1 or 2; X, Y and Z are CH or $CH_2$ groups when n is 2 and X, Y and Z are $CH_2$ or X and Y or Y and Z are CH groups forming an ethylenic linkage when n is 1 and W is hydrogen, lower alkyl, eg. methyl or ethyl, isopropyl, hydroxyethyl, vinyl or isomers, and sterioisomers thereof. Most preferred of this group is N-methyl-2-pyrrolidone. Other examples of the N-heterocyclic amide include N-methyl-2-pyridone, N-methyl-2-piperidone, 2-pyrrolidone, N-methyl-2-pyrrolone, N-isopropyl-2-pyrrolidone and isomers.
*preferably dimer The acid portion of the translocating agent is preferably 2-chloroethylphosphonic acid or the anhydride or catechol ester thereof which are readily degradable to said acid. The 2-bromoethyl, 2-iodoethyl and 2-fluoroethyl analogs of the acid and/or ester or anhydride are also contemplated as within the scope of this invention.

In preparing the translocating composition, the amide is usually mixed with the 2-haloethyl-phosphonic acid, i.e. the chloro- bromo- or iodo-ethyl phosphonic acid or the hydrolyzable derivative thereof, either directly or in a solution of one or both of the components. The resulting mixture can then be adjusted to the desired concentration for separate application to the plant or it can be added to the bioactant formulation with optional dilution, as desired for simultaneous application on the plant. The composition is conveniently applied as a separate liquid spray and may be allowed to dry on the plant before application of the plant bioactant. Normal, or less than normal, amounts of the bioactant are simultaneously or subsequently applied to obtain the desired effect. For example, herbicides are usually employed at a rate of from about ⅛ to about ⅞ of their recommended dosage, preferably from about ¼ to about ¾ of their recommended dosage when used in conjunction with the present translocating agent. Systemic fungicides and insecticides are generally employed at similarly reduced rates. Generally the bioactants are employed at ½ to about 5 pounds/acre, depending on the plant species, climatic conditions and age of the plant.

Having generally described the invention, reference is now had to the accompanying examples wherein all proportions are by weight unless otherwise indicated. The results reported in the following tables are obtained by $^{14}C$-analysis via liquid scintillation counting. It is to be understood that these examples are preferred embodiments and are not to be construed as limiting to the scope of the invention which is more properly defined in the foregoing disclosure and in the appended claims.

EXAMPLE I

Nine groups (8 per group) of Stringless Greenpod bean seeds were germinated and grown 9 days in separate flasks containing 400 ml half strength Hoagland's nutrient solution* after which, treatment with an aqueous translocating solution containing 0.5% wetting agent (Triton X 100 or Triton AG 98) and a 1:1 molar mixture of N-methyl-2-pyrrolidone (NMP) and 2-chloroethyl phosphonic acid (the acid) was effected as follows:
*An inorganic solution simulating natural soil nutrients containing $Ca(NO_3)_2.4H_2O$, $KNO_3$, $KH_2PO_4$, $MgSO_4.7H_2O$, $FePO_4$, $FeC_4H_2O_6$, $NH_4H_2PO_4$, $H_3BO_3$, $MnCl_2.4H_2O$, $ZnSO_4.7H_2O$, $CuSO_4.5H_2O$ and $H_2MoO_4.H_2O$.

Groups 2 through 4 were sprayed to drench with the translocating solution containing 500 ppm of the 1:1 molar mixture of NMP/acid; groups 5 through 7 were similarly treated with the translocating solution containing 1,000 ppm of the 1:1 molar mixture of NMP/acid and groups 8 through 10 were similarly drenched with the translocating solution containing 2,000 ppm of the 1:1 molar mixture of NMP/acid.

Simultaneously, with the translocating solution treatment, the stems of the second, fifth and eighth group of plants were injected at the cotyledonary node with 0.5 micrograms (ug), 54 millicuries per millimole (mCi/m-Mole) of 2,4,5-T-1-$^{14}C$ (i.e. 2,4,5-T having a carbon 14 tracer in the 1-position) in 1 microliter (ul) of ethanol by means of a 1 ul syringe pipette.

The seedlings of groups 3, 6 and 9 were similarly injected with 2,4,5-T-1-$^{14}C$, 4 hours after treatment with the translocating solution and seedling groups 4, 7 and 10 were similarly injected 24 hours after treatment with the translocating solution.

Four hours after injection of the herbicide, samples of each plant were collected, analyzed and results averaged and reported in following Table I. The results were highly reproducible.

Samples for analysis were prepared by wet ashing, suspension in POPOP (phenyl-oxazolyl-phenyl-oxazolyl-phenyl), and then subjected to liquid scintillation counting of the $^{14}C$ targeted 2,4,5-T in various parts of the plant and in the nutrient solution. The presence of 2,4,5-T in the nutrient solution indicates complete basipetal translocation through the plant for assured plant mortality.

TABLE I

| Effects on Translocation of 0.5g $C^{14}$ 2,4,5-T to Various Parts of Bean Seedlings[1] | | | | | | |
|---|---|---|---|---|---|---|
| Group No. | Treatment[2] | Young Shoots (%) | Primary Leaves (%) | Epicotyl (%) | Hypocotyl (%) | Roots (%) | Nutrient Solution (%) |
| | 0 hr pretreatment with Translocating solution | | | | | | |
| 2 | 500 ppm NMP/acid | 39.3 | 80.7 | 83.0 | 103.1 | 73.1 | 107.0 |
| 5 | 1000 ppm NMP/acid | 40.7 | 91.2 | 83.2 | 102.2 | 61.4 | 123.6 |
| 8 | 2000 ppm NMP/acid | 43.6 | 107.3 | 85.2 | 104.5 | 44.2 | 140.4 |
| | 4 hr pretreatment with Translocating solution | | | | | | |
| 3 | 500 ppm NMP/acid | 35.7 | 136.9 | 80.9 | 101.8 | 138.5 | 68.4 |
| 6 | 1000 ppm NMP/acid | 33.2 | 136.4 | 81.0 | 101.7 | 218.6 | 106.8 |

TABLE I-continued

| | | \multicolumn{6}{c}{Effects on Translocation of 0.5g $C^{14}$ 2,4,5-T to Various Parts of Bean Seedlings[1]} |
|---|---|---|---|---|---|---|---|
| Group No. | Treatment[2] | Young Shoots (%) | Primary Leaves (%) | Epicotyl (%) | Hypocotyl (%) | Roots (%) | Nutrient Solution (%) |
| 9 | 2000 ppm NMP/acid 24 hr pretreatment with Translocating solution | 31.4 | 139.8 | 80.3 | 101.5 | 271.2 | 131.6 |
| 4 | 500 ppm NMP/acid | 37.9 | 129.0 | 106.0 | 89.4 | 355.8 | 52.6 |
| 7 | 1000 ppm NMP/acid | 34.0 | 177.8 | 99.7 | 95.6 | 320.1 | 72.9 |
| 10 | 2000 ppm NMP/acid | 29.3 | 111.3 | 93.5 | 103.6 | 295.1 | 86.0 |

[1]Results are expressed as % of that found in controls which omit treatment with translocating agent
[2]Plants were treated with the translocating mixture at 0.4 and 24 hours prior to injection of $C^{14}$ - 2,4,5-T Gibberellic acid (GA$_3$) displayed a strong interaction with the present solution, essentially reversing the direction of translocation so that acropetal transfer to the young shoots was significantly enhanced, while basipetal transfer to the plant roots was diminished. These effects for 0.4 μg GA$_3$ added to the nutrient solutions 24 hours prior to 2,4,5-T treatment.

The above 2,4,5-T basipetal translocation improvement is observed when 2,4-D is substituted for 2,4,5-T.

The high activity of the present composition for basipetal translocation of herbicides below the point of injection is evident from the data in Table I. Additionally, a 350% increase in 2,4,5-T transfer to the plant roots was achieved at a 500 ppm NMP/acid concentration applied one day before treatment with herbicide. Significant increases in 2,4,5-T accumulation in the nutrient solution were also observed at 1,000 and 2,000 ppm NMP/acid concentration, while accumulation of 2,4,5-T in the young shoots and primary leaves was greatly reduced. In general the present translocating solution afforded faster and more complete transfer of the herbicide out of the epicotyl and hypocotyl areas of injection.

Substantially, the same improvement in basipetal translocation of 2,4,5-T and 2,4-D is observed after a 1 hour pretreatment with 2,500 ppm NMP/acid, under controlled conditions, on mixed weed species, including ragweed.

EXAMPLE II

A. Eight groups (8 per group) of Stringless Greenpod bean seeds were germinated and grown 9 days in separate flasks containing 400 ml half strength Hoagland's nutrient solution after which, treatment with an aqueous translocating solution containing 0.5% wetting agent (Triton×100 or Triton AG 98) and a 1:1 molar mixture of N-methyl-2-pyrrolidone (NMP) and 2-chloroethyl phosphonic acid (the acid) was effected as follows.

Groups 2-4 and 6-8 were sprayed to drench with the NMP/acid translocating solutions in the concentrations noted in Table II. Groups 1 and 5 were left untreated as controls.

After 23 hours, the plants in groups 1-4 were subjected to 30-40% humidity and the plants in groups 5-8 were subjected to 78-80% humidity for one hour, after which the plant stems of all groups were injected at the cotyledonary node with 0.5 micrograms (ug), 54 millicuries per millimole (mCi/mMole) of $^{14}C$ Blazer in 1 microliter (ul) of ethanol by means of a 1 ul syringe pipette.

Four hours after injection of the herbicide, samples of each plant were collected, analyzed and results averaged and reported in % of herbicide recovered from various plant parts as shown in following Table II. These results, based on liquid scintillation counting of the $^{14}C$ targeted Blazer, were highly reproducible.

Table II

| | | | \multicolumn{6}{c}{EFFECT OF HUMIDITY ON DISTRIBUTION BLAZER 4 HOURS AFTER INJECTION} |
|---|---|---|---|---|---|---|---|---|
| | | Trans. | \multicolumn{6}{c}{% of Total Recovered} |
| Plant Group | Humidity % | Agent (ppm) | Young Shoot | Primary Leaves | Epicotyl | Treated Area | Hypocotyl | Root |
| 1 | 30-40 | 0 | 3.0 | 11.2 | 12.4 | 26.2 | 7.7 | 1.4 |
| 2 | " | 500 | 1.7 | 12.6 | 10.7 | 20.8 | 6.4 | 3.6 |
| 3 | " | 1000 | 1.3 | 8.8 | 9.2 | 26.4 | 7.4 | 5.5 |
| 4 | " | 1500 | 1.2 | 12.6 | 9.7 | 20.7 | 8.7 | 5.5 |
| 5 | 70-80 | 0 | 4.0 | 13.5 | 15.2 | 24.3 | 8.8 | 1.4 |
| 6 | " | 500 | 1.1 | 15.5 | 12.0 | 20.2 | 9.7 | 4.2 |
| 7 | " | 1000 | 0.7 | 12.9 | 9.7 | 21.0 | 10.9 | 4.7 |
| 8 | " | 1500 | 0.4 | 15.8 | 9.6 | 14.7 | 9.8 | 6.3 |

The above data shows that basipetal translocation of Blazer was increased more than 400% by the use of the present translocating agent. It was also noted at the higher humidity, that a small increase in acropetal translocation to primary leaves was achieved along with the major basipetal translocation. Thus, translocation in both directions was, in this instance, improved.

B. Above Example II A. was repeated under average 40% humidity conditions, except that $^{14}C$-glyphosate was substituted for $^{14}C$ Blazer. The results of these experiments are reported in following Table III.

TABLE III

| Plant Group | Transloc. Agent (ppm) | Young Shoot | Primary Leaves | Epicotyl | Treated Area | Hypocotyl | Root | Nutrient Solution |
|---|---|---|---|---|---|---|---|---|
| | | | | % of Total Recovered | | | | |
| 9 | 0 | 13.8 | 60.5 | 4.4 | 13.4 | 2.6 | 5.3 | 0.05 |
| 10 | 250 | 7.0 | 64.1 | 3.4 | 16.1 | 2.6 | 7.0 | 0.04 |
| 11 | 500 | 3.9 | 65.7 | 3.8 | 20.4 | 2.7 | 7.3 | 0.14 |
| 12 | 2000 | 1.4 | 58.7 | 3.3 | 20.9 | 3.3 | 12.3 | 0.04 |

In the above table, simultaneous treatment with translocating agent and $C^{14}$ Glyphosate, under the given conditions, resulted in more complete exhaustion of herbicide from the treated area, probably due to the increased time between injection and analysis of the samples. However, basipetal translocation remained about the same; whereas acropetal translocation to the primary leaves increased. All other acropetal translocation remained at about the same reduced level as found in groups 10–12 above.

C. Example II A, above, is repeated under average 40% humidity conditions, except that $C^{14}$-dicamba was substituted for $C^{14}$-Blazer. However, in these tests, simultaneous treatment with herbicide and translocating agent was compared with herbicidal treatment applied 24 hours after spraying with the translocating agent. The results of these experiments are reported in following Table IV.

TABLE IV

| Plant Group | Treatment | Transloc. Agent (ppm) | Young Shoot | Primary Leaves | Epicotyl | Treated Area | Hypocotyl | Root | Nutrient Solution |
|---|---|---|---|---|---|---|---|---|---|
| | | | | | % of Total Recovered | | | | |
| 13 | Simultaneous | 250 | 28.0 | 21.1 | 14.1 | 26.1 | 7.5 | 2.8 | 1.2 |
| 14 | " | 500 | 15.7 | 20.4 | 16.4 | 34.2 | 9.4 | 2.2 | 1.7 |
| 15 | " | 2000 | 14.5 | 29.1 | 8.6 | 28.3 | 14.7 | 2.2 | 2.4 |
| 16 | | 0 | 34.1 | 18.2 | 14.7 | 25.6 | 6.4 | 1.7 | 1.3 |
| 17 | 24 hrs, Pretreat. | 250 | 13.9 | 22.4 | 15.9 | 30.4 | 12.1 | 3.1 | 2.0 |
| 18 | " | 500 | 11.5 | 31.0 | 15.6 | 26.5 | 11.5 | 4.8 | 1.3 |
| 19 | " | 2000 | 7.8 | 15.9 | 15.7 | 37.1 | 14.8 | 6.4 | 4.1 |

Table IV like Table II, also illustrates an increase in acropetal translocation to the primary leaves in addition to the major basipetal translocation to the hypocotyl and roots when using the present translocating agent. Accordingly, while the major effect is a basipetal transport of bioactant, this can be accompanied by acropetal transfer to provide enhanced general translocation in the plant.

EXAMPLE III

Bean seedlings grown as described in Example II A. were sprayed with aqueous solutions containing 2000 ppm NMP/ethephon wherein the molar ratios of acid to NMP were varied as shown in Table V. A separate group of bean seedlings were not sprayed as a control. All plants were injected with 0.5 μg $^{14}C$-2,4,5-T 4 hours after spraying with the translocation agent as described above and plant parts were collected 4 hours after injection for analysis in accordance with the method described in Example II A. The results of these experiments are reported in Table V.

TABLE V

| Plant Group | Ethephon: NMP | Young Shoots | Primary Leaves | Epicotyl | Treated Area | Hypocotyl | Root | Nutrient Solution |
|---|---|---|---|---|---|---|---|---|
| | | | | % of Total Recovered | | | | |
| 20 | 1:1 | 1.5 | 12.7 | 27.8 | 39.5 | 16.0 | 2.3 | 0.3 |
| 21 | 2:1 | 1.6 | 9.1 | 24.8 | 44.5 | 17.2 | 2.3 | 0.5 |
| 22 | 3:1 | 1.4 | 9.1 | 25.6 | 39.9 | 20.9 | 2.6 | 0.5 |
| 23 | 4:1 | 1.7 | 12.2 | 24.9 | 41.9 | 16.8 | 2.0 | 0.4 |
| 24 | 1:2 | 1.6 | 10.6 | 25.3 | 40.7 | 20.0 | 1.8 | 0.4 |
| 25 | 1:3 | 0.8 | 11.9 | 22.9 | 45.0 | 16.1 | 3.0 | 0.5 |
| 26 | 1:4 | 1.8 | 9.2 | 25.1 | 41.0 | 19.2 | 3.3 | 0.5 |
| 27 | 0:0 | 2.5 | 8.3 | 26.8 | 43.0 | 18.9 | 1.6 | 0.3 |

EXAMPLE IV

The treatment of Example I, group 10 was repeated on pea seedlings except that Tricontanol is substituted for 2,4,5-T. Plants conditioned with the translocating solution visibly matured to pod set about one week before those treated with 1.2 times the amount Tricontanol alone; indicating more rapid translocation and moe efficient utilization with 1/5 the amount of Tricontanol plant growth promoter.

EXAMPLE V

Field bindweed plants were grown from 10 cm root sections taken from mature plants in the field. The plants were grown in 400 ml at ½ strength Hoagland's nutrient solution until there were 5 to 7 fully expanded leaves on each plant at which time they were sprayed with a foliar application of 2,000 ppm 1:1 molar NMP/acid containing 0.05% Triton B 1956 as a wetting agent. As soon as the spray was applied, the plants were separately treated on a mature leaf with four 2.5 μl drops of ethanol containing a total of 1 μg of $^{14}C$-dicamba (17.06 mCi/mMole, ring-UL) and with 8.7 μg of $^{14}C$-glyphosate (1.95 mCi/mMole, methyl-$^{14}C$). The field bindweed plants were harvested at 24 hours after treatment.

The treatments were replicated eight times for dicamba and six times for glyphosate. The plant parts were freeze-dried after harvesting and $^{14}C$ was analyzed by liquid scintillation counting. Table VI reports the results of these experiments.

TABLE VI

Effects on translocation with simultaneous application of glyphosate
(Roundup) or dicamba (Banvel) on field bindweed.

| Treatment | Upper foliage (%) | Original root (%) | Translocation* Upper root (%) | Lower root (%) | Total root (%) | Nutrient (%) |
|---|---|---|---|---|---|---|
| Dicamba + NMP/acid | 68.7 | 222.9 | 248.2 | 246.3 | 231.1 | 181.9 |
| Glyphosate + NMP/acid | 46.9 | 95.0 | 264.4 | 141.1 | 143.3 | 77.4 |

*The values are expressed as a % of the control omitting treatment with translocating agent. The dicamba or glyphosate were applied simultaneously with the NMP/ethephon. All plants were harvested 24 hours following treatment.

As shown in Table VI foliar treatments with the present translocating solution also had significant effects on the basipetal transfer of dicamba and glyphosate in field bindweed. Translocation of dicamba to the roots was increased by as much as 230% while translocation of glyphosate to roots was increased by 143%. In these experiments the present solution was applied simultaneously with the herbicides.

EXAMPLE VI

Matured mesquite trees, growing on several acres, were hand sprayed to run-off, at an average temperature of 85° F. and an average humidity of 40% with various aqueous solutions containing 100 or 50 ppm of herbicide and 50–1,000 ppm translocating agent as indicated in Table VII. The various aqueous solutions were sprayed at a rate of 100 gals./acre. The specific agents and herbicides in the concentrations employed are also reported in the table.

One year after treatment the trees were observed and evaluated on a % mortality (no regrowth) basis. Results are reported in Table VII and are based on 5 replicates.

The analysis did not include a breakdown of acropetal vs. basipetal translocation of the herbicide; thus, the % mortality is the result of total herbicidal translocation in the plant. Nevertheless, it is evident that herbicidal translocation was significantly increased by use of the translocating agent.

TABLE VII

TRANSLOCATION OF HERBICIDES
MESQUITE MORTALITY

| Herbicide | Translocating Agent:NMP/Ethephon* | % Mortality |
|---|---|---|
| 50 ppm NMP/Ethephon | — | 0 |
| 100 ppm NMP/Ethephon | — | 0 |
| 250 ppm NMP/Ethephon | — | 0 |
| 500 ppm NMP/Ethephon | — | 0 |
| 1000 ppm NMP/Ethephon | — | 0 |
| 100 ppm 2,4,5-T amine | — | 40 |
| 100 ppm 2,4,5-T amine | +50 ppm | 60 |
| 100 ppm 2,4,5-T amine | 100 ppm | 50 |
| 100 ppm 2,4,5-T amine | 250 ppm | 20 |
| 100 ppm 2,4,5-T amine | 500 ppm | 25 |
| 100 ppm 2,4,5-T amine | 1000 ppm | 0 |
| 50 ppm 2,4,5-T amine | — | 0 |
| 50 ppm 2,4,5-T amine | +50 ppm | 66 |
| 50 ppm 2,4,5-T amine | 100 ppm | 40 |
| 50 ppm 2,4,5-T amine | 250 ppm | 40 |
| 50 ppm 2,4,5-T amine | 500 ppm | 25 |
| 50 ppm 2,4,5-T amine | 1000 ppm | 50 |
| 100 ppm Tordon 225 E | — | 80 |
| 100 ppm Tordon 225 E | +50 ppm | 20 |
| 100 ppm Tordon 225 E | 100 ppm | 80 |
| 100 ppm Tordon 225 E | 250 ppm | 100 |
| 100 ppm Tordon 225 E | 500 ppm | 100 |
| 100 ppm Tordon 225 E | 1000 ppm | 50 |
| 50 ppm Tordon 225 E | — | 0 |
| 50 ppm Tordon 225 E | +50 ppm | 100 |
| 50 ppm Tordon 225 E | 100 ppm | 60 |
| 50 ppm Tordon 225 E | 250 ppm | 50 |
| 50 ppm Tordon 225 E | 500 ppm | 80 |
| 50 ppm Tordon 225 E | 1000 ppm | 60 |

COMPARISON OF TRANSLOCATION WHEN SUBSTITUTING ETHEPHON FOR NMP/ETHEPHON 1:1 MIXTURE

| Herbicide | Chemical Additive:Ethephon | % Mortality |
|---|---|---|
| 50 ppm Ethephon | — | 0 |
| 100 ppm Ethephon | — | 0 |
| 250 ppm Ethephon | — | 0 |
| 500 ppm Ethephon | — | 0 |
| 1000 ppm Ethephon | — | 0 |
| 100 ppm 2,4,5-T amine | +50 ppm | 50 |
| 100 ppm 2,4,5-T amine | 100 ppm | 20 |
| 100 ppm 2,4,5-T amine | 250 ppm | 0 |
| 100 ppm 2,4,5-T amine | 500 ppm | 0 |
| 100 ppm 2,4,5-T amine | 1000 ppm | 0 |
| 50 ppm 2,4,5-T amine | +50 ppm | 20 |
| 50 ppm 2,4,5-T amine | 100 ppm | 0 |
| 50 ppm 2,4,5-T amine | 250 ppm | 25 |
| 50 ppm 2,4,5-T amine | 500 ppm | 40 |
| 50 ppm 2,4,5-T amine | 1000 ppm | 20 |
| 100 ppm Tordon 225 E | +50 ppm | 0 |
| 100 ppm Tordon 225 E | 100 ppm | 20 |
| 100 ppm Tordon 225 E | 250 ppm | 60 |
| 100 ppm Tordon 225 E | 500 ppm | 0 |
| 100 ppm Tordon 225 E | 1000 ppm | 40 |
| 50 ppm Tordon 225 E | +50 ppm | 40 |
| 50 ppm Tordon 225 E | 100 ppm | 25 |
| 50 ppm Tordon 225 E | 250 ppm | 60 |
| 50 ppm Tordon 225 E | 500 ppm | 50 |
| 50 ppm Tordon 225 E | 1000 ppm | 40 |

In the case of 2,4,5-T ester, NMP improves translocation when less than optimum amounts of the ester (less than 50 ppm) are employed.

EXAMPLE VII

Half of the plants in two fifty foot rows of matured woolly bursage (37 plants/m$^2$) were sprayed with aqueous solutions containing 2,000 ppm of an NMP/ethephon 1:1 molar mixtures and an equal number of plants were left untreated.

After 24 hours, all plants were treated with aqueous solutions of the bioactants (1 part to 2 parts of water) reported in Table VIII by means of a ropewick applicator, so that plant were contacted with about 30 ppm of herbicide. A separate group of plants was left untreated by either the translocating agent or the bioactant, as a control.

After one month, control of the bursage was noted and reported in the following table.

TABLE VIII

| Bioactant | Translocation Agent | % Control of Bursage |
|---|---|---|
| Dicamba | — | 73 |
| Roundup | — | 60 |
| Tordon | — | 67 |
| Dicamba + Tordon (part/part) | — | 60 |
| Dicamba + Roundup (part/part) | — | 63 |
| Roundup + Tordon (part/part) | — | 80 |
| Dicamba | + NMP/ethephon | 93 |

TABLE VIII-continued

| Bioactant | Translocation Agent | % Control of Bursage |
| --- | --- | --- |
| Roundup | + NMP/ethephon | 97 |
| Tordon | + NMP/ethephon | 93 |
| Dicamba + Tordon (part/part) | + NMP/ethephon | 93 |
| Dicamba + Roundup (part/part) | + NMP/ethephon | 100 |
| Roundup + Tordon (part/part) | + NMP/ethephon | 97 |
| Control | — | 0 |

It is to be understood that any of the aforedescribed herbicides, plant growth promoters, or inhibitors, nutrients or systemic insecticides and fungicides can be substituted in the above examples to provide more rapid and complete translocation in the plant and more efficient use of the bioactant.

What is claimed is:

1. A basipetal-enhanced, herbicidal, translocating composition consisting essentially of a phytotoxic amount of a postemergent herbicide and a basipetal-promotional translocating and phytotoxic increasing amount of a basipetal-promotional translocating agent consisting essentially of a mixture of N-methylpyrrolidone or polyvinylpyrrolidone and a 2-haloethylphosphonic acid combined in a mole ratio between about 1:5 and about 10:1.

2. The composition of claim 1 wherein said translocating agent is a mixture of N-methyl-2-pyrrolidone and 2-chloroethylphosphonic acid.

3. The process of contacting a plant with a postemergent herbicide and a translocating agent of claim 1 in an amount effective to promote basipetal translocation of said herbicide and to increase the phytotoxic effect of said postemergent herbicide.

4. The process of claim 3 wherein the translocating agent is an aqueous solution of a mixture of N-methyl-2-pyrrolidone and 2-chloroethylphosphonic acid combined in a mole ratio of from about 1:5 to about 10:1.

* * * * *